(12) United States Patent
Fahy et al.

(10) Patent No.: US 6,949,335 B2
(45) Date of Patent: *Sep. 27, 2005

(54) POLYGLYCEROL AND LACTOSE COMPOSITIONS FOR THE PROTECTION OF LIVING SYSTEMS FROM STATES OF REDUCED METABOLISM

(75) Inventors: Gregory M. Fahy, Corona, CA (US); Jun Wu, Rancho Cucamonga, CA (US)

(73) Assignee: 21st Century Medicine, Inc., Rancho Cucamonga, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/066,285

(22) Filed: Feb. 1, 2002

(65) Prior Publication Data

US 2003/0027924 A1 Feb. 6, 2003

Related U.S. Application Data

(63) Continuation-in-part of application No. 09/916,396, filed on Jul. 27, 2001, now Pat. No. 6,869,757, and a continuation-in-part of application No. 09/726,857, filed on Nov. 30, 2000, now Pat. No. 6,616,858.
(60) Provisional application No. 60/221,691, filed on Jul. 31, 2000, and provisional application No. 60/167,963, filed on Nov. 30, 1999.

(51) Int. Cl.[7] .............................. A01N 1/00; A01N 1/02
(52) U.S. Cl. .......................... 435/1.1; 435/1.2; 435/1.3
(58) Field of Search .......................... 435/1.1, 1.2, 1.3

(56) References Cited

U.S. PATENT DOCUMENTS

| 5,145,769 A | 9/1992 | McNally et al. |
| 5,158,867 A | 10/1992 | McNally et al. |
| 5,306,711 A | 4/1994 | Andrews |
| 6,194,137 B1 * | 2/2001 | Khirabadi et al. ........... 435/1.3 |
| 6,616,858 B2 * | 9/2003 | Fahy et al. ................... 252/70 |

OTHER PUBLICATIONS

Klebe et al., "Identification of new cryoprotective agents for cultured mammalian cells", In Vitro 19 (3): 167–170 (1983).*
Al–Abdulla, Nael A. B.Sc. et al., The Effects of Supercooling Chemicals on Myocardial Ultrastructure: A Transmission Electron Microscopy Case Study, *Connecticut Medicine*, 59: 387–399, 1995.
Kaufman, Herbert E. et al., Optisol Corneal Storage Medium, *Arch Ophthalmol*, 109: 864–868, 1991.
Toledo–Pereyra, Luis H. and Ramakrishnan, Vellore R., Effect of Chondroitin Sulfate on the Prolongation of Kidney Allograft Survival, *Transplantation*, 27 (6): 427–429, 1979.
Pegg, D.E., Jacobsen, I.A., Halasz, N.A., Organ Preservation—Basic and Applied Aspects, *MTP Press*, Lancaster, 1982, pp. 323–324.
Khirabadi, Bijan S. and Fahy, Gregory M., Cryopreservation of the Mammalian Kidney. 1. Transplantation of Rabbit Kidneys Perfused with EC and RPS–2 at 2–4° $C^1$, *Cryobiology*, 31: 10–25, 1994.
Fahy, Gregory M. et al., Cell Biology of Trauma, J.J. Lemasters and C. Oliver (Eds.), *CRC Press*, 1995, pp. 333–356.

* cited by examiner

*Primary Examiner*—Sandra E. Saucier
(74) *Attorney, Agent, or Firm*—Foley & Lardner; Stephen E. Reiter (57) ABSTRACT

Polyglycerol, lactose, and a combination of polyglycerol and lactose are effective at preserving cells, tissues, and organs from damage due to hypothermic, ischemic, or other metabolic impairment, and a mixture of polyglycerol plus lactose is particularly useful for the hypothermic storage of cells, tissues, and organs. The mixture of polyglycerol and lactose can be further improved by the addition of chondroitin sulfate, chlorpromazine, calcium, citrate, glutathione, adenine, glucose, magnesium, and a pH buffer.

32 Claims, 5 Drawing Sheets

POLYGLYCEROL AND LACTOSE COMPOSITIONS FOR THE PROTECTION OF LIVING SYSTEMS FROM STATES OF REDUCED METABOLISM

RELATED APPLICATIONS

This application is a Continuation in Part of U.S. patent application Ser. No. 09/726,857, filed Nov. 30, 2000, now U.S. Pat. No. 6,616,858, which claims priority under 35 U.S.C. §119 of U.S. Provisional Application No. 60/167,963, filed Nov. 30, 1999 (herein incorporated by reference). This application is also a Continuation in Part of U.S. patent application Ser. No. 09/916,396, filed Jul. 27, 2001, now U.S. Pat. No. 6,869,757, which claims priority under 35 U.S.C. §119 of U.S. Provisional application No. 60/221,691, filed Jul. $31^{st}$, 2000, all of which are herein incorporated by reference.

FIELD OF THE INVENTION

This invention relates generally to the field of cell, tissue, and organ preservation. More specifically, this invention relates to the field of protection of cells, tissues, and organs from states such as hypothermia. Still more specifically, this invention relates to the use of polyglycerol and other solutes, especially alpha lactose, for protecting living systems during periods of depressed metabolism, with or without supercooling.

BACKGROUND OF THE INVENTION

The current shortage of organs for transplantation mandates that maximum usage be obtained from the scarce resource represented by vital organs. Despite this imperative, many organs that could be transplanted are not transplanted due to limitations on the useful lifetime of organs after they are removed from the body. Thus, there is clearly a need for better preservation solutions for vital organs.

Many preservation solutions have been proposed and patented in the prior art. However, the primary solution used worldwide for most transplantable organs is UW Solution, also known as VIASPAN™, the trade name under which it was initially sold by DuPont Pharmaceuticals. There is no alternative solution that is generally regarded as being superior to UW Solution. Therefore, to be useful, any new organ preservation solutions should be at least competitive with UW Solution.

Despite its widespread use, there is much dissatisfaction with UW Solution as an organ preservation solution. First of all, it requires the addition of expensive additives prior to use, which is inconvenient. Second, UW has to be washed out prior to transplantation of the preserved organ, which is also inconvenient and wastes valuable operating room time. Third, UW solution is viscous and sticky and therefore does a poor job of washing blood out of organs that are flushed with it. To respond to this problem, many centers flush out the blood with a different solution and then flush out this intermediate solution with UW, again wasting time and solution. Alternatively, blood remaining in the organ may account for the failure of a large fraction of transplanted kidneys to function immediately upon transplantation. Fourth, kidneys preserved with UW Solution by simple cold storage for over 24 hours are sufficiently damaged to offset the advantages of organ sharing for improving tissue matching between donor and recipient. Tissue matching is known to have major effects on survival rates five to ten years following transplantation. Therefore, improved preservation after 24 hours of storage could translate into expanded use of well-matched organ transplants and improved long-term survival of organ recipients. This in turn would mean the need for fewer re-transplants after rejection, which would free up the otherwise-needed organs for other recipients.

The limitations and poor efficacy of UW and other organ preservation solutions for preservation for 24 hours and beyond indicate the need for an improved solution.

SUMMARY OF THE INVENTION

The present invention is a preservation solution for cells, tissues, and organs comprising a combination of polyglycerol and lactose in an amount effective to preserve said cells, tissues, and organs under hypothermic and other reduced-metabolism conditions. In one embodiment the lactose is alpha lactose. In a further embodiment, the polyglycerol is from n=2 to n=200 monomers. In a further embodiment, the polyglycerol is decaglycerol or hexaglycerol. The lactose is preferably at a concentration from about 11 mM to 250 mM, or more preferably at about 20–150 mM. The polyglycerol is preferably at a concentration of 10 mOsm to 250 mOsm (about 0.3% w/v to about 7.3% w/v, respectfully, for decaglycerol), or more preferably from about 20–200 mOsm. In a further embodiment, the preservation solution may additionally contain chondroitin sulfate, preferably at a concentration of about 0.01% w/v to 1% w/v. In a further embodiment, the preservation solution may additionally contain chlorpromazine, preferably at a concentration of about 1–50 micrograms/ml, even more preferably at about 2–10 micrograms/ml. The sum of lactose + polyglycerol osmolality is preferably from 20–250 mOsm.

In an alternative embodiment, the preservation solution may also contain one or more of: calcium, citrate, glutathione, NaCl, at least one buffer, such as a phosphate buffer, glucose, adenine, magnesium, and acetate.

In one embodiment, the solution has an osmolality of less than about 350 mOsm. In a further embodiment, the sum of all impermeant species contributes 20–250 mOsm (milliosmolal) to the osmolality of the solution.

A further embodiment is a method for the preservation of cells, tissues, or organs under conditions of impaired cell volume homeostasis in addition to hypothermia below 10° C., which method involves contacting the cells, tissues, or organs with a solution comprising polyglycerol in an amount effective to preclude or to reverse cell swelling. The contacting may be via intravenous or intra-arterial administration. The contacting may be in vivo via arterial organ perfusion or retrograde venous perfusion of an organ or vascularized tissue. Alternatively, the contacting may be in vitro via arterial organ perfusion or retrograde venous perfusion of an organ or vascularized tissue. In one embodiment, the contacting is via the immersion of or bathing of affected cells, tissues, or organs. The polyglycerol is preferably from n=2 to 200 monomer units in length and may be tetraglycerol, hexaglycerol, or decaglycerol. Preferably the polyglycerol is at a concentration of from about 20 mOsm to 1,500 mOsm when in contact with said cell, tissue, or organ. The preservation solution may also comprise lactose. In one embodiment, the lactose is alpha lactose.

In a further embodiment, the effective amount is an isotonic solution. Alternatively, the effective amount is a hypertonic solution.

One embodiment is a method for preserving cells, tissues, or organs under conditions of impaired cell volume homeostasis by contacting the cells with a solution comprising polyglycerol in an amount effective to preclude or to reverse cell swelling.

BRIEF DESCRIPTION OF THE DRAWINGS

These and other features, aspects and advantages of the present invention will now be described with reference to the drawings of the preferred embodiment, which embodiment is intended to illustrate and not to limit the invention, and in which.

DETAILED DESCRIPTION OF THE PREFERRED EMBODIMENT

Polyglycerol (PGL) is a water-soluble, non-toxic, FDA-approved, low molecular weight polymer given by the formula PGL is commercially available with n=2 (diglycerol) up to n=10 (decaglycerol) and beyond. For tetraglycerol, n=4, and for hexaglycerol, n=6. The molecular mass of decaglycerol is about 758 daltons.

PGL is an inexpensive, non-toxic compound used in cosmetics and in esterified form as a food additive that can replace more than 50% of fat calories in some food (Babayan, J. Environ. Pathol. Toxicol. Oncol. 6: 15–24, 1986). Inside the body, PGL esters are metabolized back into PGL, which underscores the non-toxic nature of this compound. Consumers of MACDONALD'S donuts and birthday cakes, WEIGHT WATCHER'S ice cream, dietetic desserts and chocolate emulsified with polyglycerol polyricinoleic acid, for example, have PGL released into their bodies without negative consequences.

Although this molecule was heretofore used only in the food industry as a sweetener and fat substitute, it was surprisingly found by one of the present inventors to possess the ability to prevent nucleation of ice in supercooled solutions (U.S. patent application Ser. No. 09/726,857). Given the potential usefulness of supercooling for the preservation of cells, tissues, organs, and proteins near 0° C. (see, for example, Conn. Med. 59, pp. 387–99, 1995— herein incorporated in its entirety by reference thereto), it became of interest to know whether PGL could also support the viability of cells, tissues, and organs at temperatures in the vicinity of 0° C.

One of the cornerstones of organ preservation solutions is non-toxic impermeants. The impermeants of UW Solution are raffinose, hydroxyethyl starch, and either lactobionate or gluconate. Although many other impermeants have been proposed and tested, there is no generally accepted impermeant known that is superior to the impermeants of UW Solution. It is an object of the present invention to provide solutions for the superior protection of living cells, tissues, and organs, said solutions having polyglycerol and/or lactose, in which, when combined, the proportion of polyglycerol to lactose may vary from 1:0 to 0:1, but in which the ratio of the osmolality of polyglycerol to that of lactose is most preferably in the range of 0.2 to 10.

Lactose is a disaccharide composed of galactose and glucose. In nature, it is found only in milk. Because milk is produced in industrial quantities in the United States, rather pure alpha-lactose can be purchased for as little as $9.90 per kilogram (Sigma Chemical 1999 catalogue number L 3625), making it even less costly than sucrose. Other forms of lactose (beta lactose, D-lactose, and allolactose) are also envisioned to be effective, but are more costly than alpha lactose.

Lactose has never been explored as a component of an organ preservation solution, and no information on its suitability was available until the present disclosure. Lactose is a reducing sugar, which previously might have made it seem undesirable. Further, UW Solution contains raffinose, a trisaccharide costing over $2000/kg, and has been sold commercially worldwide for over 15 years despite the price differential between raffinose and lactose. Clearly, this indicates that using lactose in place of a higher molecular mass sugar such as raffinose or in place of the charged impermeants such as lactobionate or gluconate was not previously contemplated. This is logical based on a) the rational belief in the prior art that a disaccharide will be inferior to a trisaccharide in its ability to preclude hypothermic cell swelling, and b) the observation of many investigators that raffinose does not compete with lactobionate in importance in UW Solution, the raffinose being dispensable without harm, in contrast to the indispensability of lactobionate. Further, as is described in FIG. 1 below, sucrose, the most popular disaccharide, was less effective than the monosaccharide, glucose, in supporting the viability of rabbit renal cortical slices during prolonged cold storage, despite the fact that it is a non-reducing disaccharide as opposed to glucose, which is a reducing monosaccharide. The latter observation demonstrates that the efficacy of sugars for cold storage solutions cannot be predicted, and must be determined experimentally. The choice of lactose has never been contemplated in the prior art for use in cell preservation or protection.

Polyglycerol and alpha lactose are non-toxic molecules that are unable to cross the cell membrane under hypothermic conditions and therefore are capable of arresting cell swelling during cell, tissue, or organ storage. Furthermore, polyglycerol is expected to be impermeable even at elevated temperatures, such as normal body temperature (37° C.), and therefore will protect cells, tissues, organs, and organisms from high temperature states of reduced metabolism or reduced cell volume regulatory ability, such as in ouabain poisoning, warm ischemia, shock, heat stroke, or cardiac arrest. Alpha lactose, polyglycerol, and the combination thereof are also useful for protecting organs during cooling, warming, and holding (for example, during transplantation) and may also be efficacious for preservation by perfusion or intermittent perfusion as opposed to simple static storage.

It is not predictable that the combination of a disaccharide with the larger decaglycerol molecule would improve the efficacy of decaglycerol for inhibition of cell damage during cold storage, since decaglycerol alone should be fully sufficient for this role, and lactose should have no added benefit. Nevertheless, surprisingly, the combination of alpha lactose and decaglycerol is more efficacious than the use of decaglycerol alone when essentially equi-osmotic concentrations of decaglycerol or decaglycerol plus lactose are compared. By supplying polyglycerol in combination with lactose, with or without other appropriate molecules needed for the support of cellular viability and organ function, formulas are provided that permit cells, tissues and organs to be preserved, for example, for at least 48 hours of static cold storage at 0° C. without the need to add expensive ingredients before use or to remove the preservative solution from the organ before transplantation. A range of effective concentrations of polyglycerol, alpha lactose, and other important components is provided.

In addition to polyglycerol and alpha lactose, additional valuable components include chondroitin sulfate and chlorpromazine. Chondroitin sulfate is a connective tissue polysaccharide never before contemplated for use in organ preservation solutions. It has been used in high concentrations to preserve corneas (e.g., "Optisol" contains 2.5% w/v chondroitin sulfate [Arch. Ophthalmol. 109: 864–868, 1991]), and it has been used as a cryoprotectant (an agent that protects against damage incurred by freezing and thawing) in blood vessel segments submerged in a cryoprotectively effective concentration of glycosaminoglycans in combination with a cell penetrating cryoprotectant in a medium for freezing blood vessels (U.S. Pat. Nos. 5,145,769 and 5,158,867), but it has never been considered to improve the preservation of whole organs during hypothermic storage. In a 1994 U.S. patent (U.S. Pat. No. 5,306,711), for example, Peter Andrews reviews cornea preservation media, listing their contents of chondroitin sulfate, but then claims organ preservation solutions devoid of chondroitin sulfate, showing the lack of obviousness of including this agent in an organ preservation solution. Chondroitin sulfate was used in one paper in 1979 in an attempt to modify immunogenicity after kidney transplantation (L. H. Toledo-Pereyra and V. R. Ramakrishnan, Transplantation 27(6):427–9, 1979), but these authors found no reduction of hypothermic preservation injury using 0.025% chondroitin sulfate, stating "there were no significant functional differences between the control and CIS [chondroitin sulfate]-treated groups," which teaches away from the use of chondroitin sulfate in organ preservation perfusates or flush solutions. We believe these experiments used a preservation model that was not appropriate for demonstrating beneficial effects of chondroitin sulfate or any other improvement in organ preservation solutions. In the present invention, the most preferred concentrations of chondroitin sulfate are 0.1–0.5% w/v, concentrations that are far lower than the concentrations used for cornea hypothermic preservation or blood vessel freezing (2.5% w/v).

Jabcobsen (Organ Preservation, Basic and Applied Aspects, D. E. Pegg, I. A. Jacobsen, and N. A. Halasz, editors, MTP Press, Lancaster, 1982, page 324) found that chlorpromazine incorporation into a storage solution for rabbit kidneys was lethal after 24–48 hrs of storage when chlorpromazine was used at a concentration of 15 micrograms/ml. Therefore, the ability of chlorpromazine to strongly improve the efficacy of the current invention at a concentration of, for example, 5 micrograms/ml is most surprising. Because the use of chlorpromazine is believed to be unnecessary when good preservation solutions are used, or if chlorpromazine is given to the donor before organ collection (see Organ Preservation, Basic and Applied Aspects, D. E. Pegg, I. A. Jacobsen, and N. A. Halasz, editors, MTP Press, Lancaster, 1982, pages 323–324), the value of including chlorpromazine in an organ preservation solution has not been recognized for the past 20 years or so.

RPS-2 is an excellent solution for static (non-perfusional) storage of kidney slices and whole rabbit kidneys for relatively limited periods (see for example Khirabadi and Fahy, Cryobiology 30: 10–25, 1994). Although RPS-2 causes no cellular injury as judged by sodium and potassium transport capacity following cold storage for up to 4 days, its reliance on glucose as the main impermeant permits cell swelling even after 24 hrs of cold storage, and therefore it is not ideal for long term whole organ cold storage. By replacing glucose in RPS-2 with less permeable species, a first test of the acceptability of such species based on lack of impairment of ion translocation following storage can be obtained.

Figure 1:
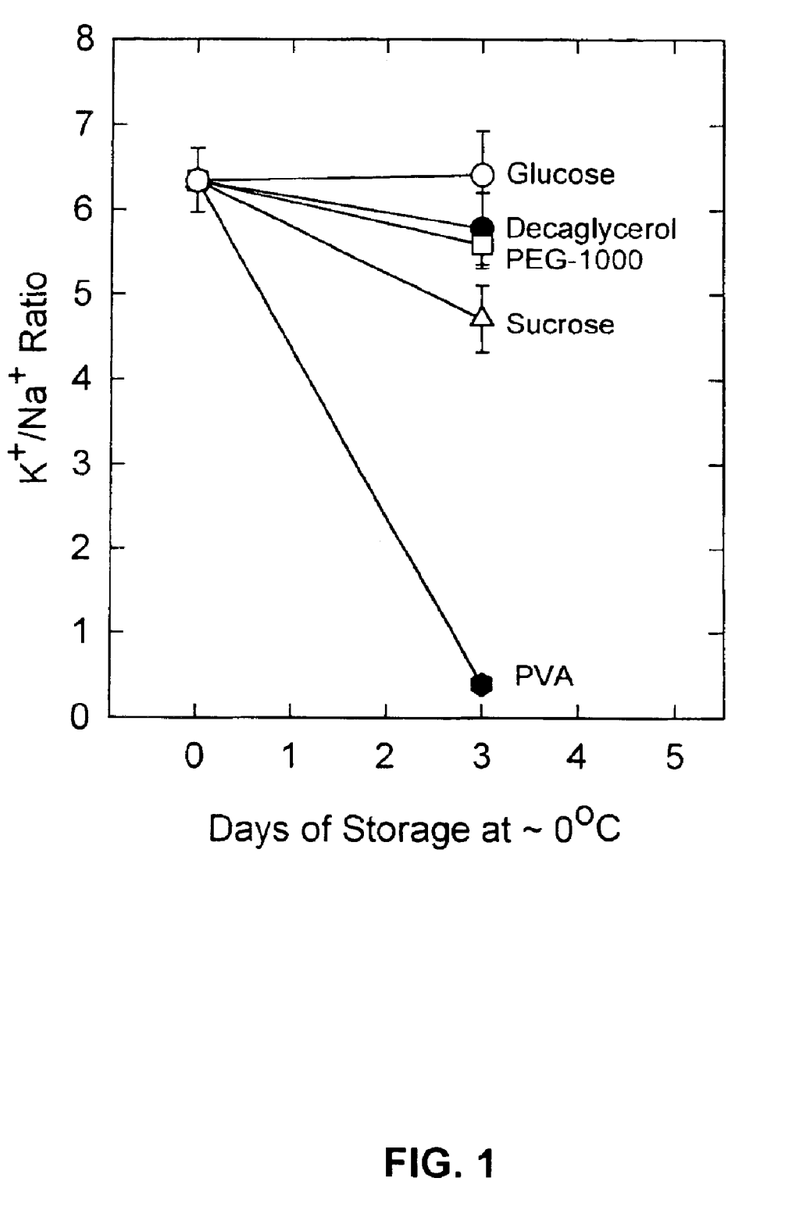
FIG. 1 shows the lack of toxicity of PGL as used in an organ preservation solution in place of glucose for preservation of kidney slices.

As described in U.S. patent application Ser. No. 09/726, 857, (herein incorporated by reference), PGL can be used for prolonged tissue slice preservation in a conventional 0° C. organ flush/cold storage solution without detrimental effects, showing the utility of PGL for either storage below 0° C. or for conventional storage at 0 to 10° C. As shown in FIG. 1, kidney slices stored in RPS-2 (curve labeled "Glucose", open circles) could be stored for 3 days near 0° C. with no demonstrable deterioration based on their subsequent ability to accumulate potassium and to extrude sodium during incubation in Cross-Taggart solution (see Fahy et al., in "Cell Biology of Trauma", J. J. Lemasters and C. Oliver, Eds., CRC Press, 1995, pp. 333–356, and citations therein, for the precise methodology of the functional assay). RPS-2 contains 180 mM glucose as a major component (and also includes 7.2 mM $K_2HPO_4$, 1 mM $CaCl_2$, 2 mM $MgCl_2$, 5 mM reduced glutathione, 28.2 mM KCl, 10 mM $NaHCO_3$, and 1 mM Adenine HCl). When 170 mM glucose was replaced with an osmotically equivalent amount of decaglycerol (black circles, curve labeled "decaglycerol"), there was no significant difference between the $K^+/Na^+$ ratio obtained and the ratio obtained without glucose replacement (p>0.05). Polyethylene glycol of mean molecular mass ~1000 daltons (PEG-1000, open boxes) also yielded good results, whereas sucrose (open triangles) was distinctly inferior, and polyvinyl alcohol (black hexagons) was overtly toxic. It is expected that PGL containing at least 2 glycerol monomers (n>=2) will be effective for prevention of at least short-term (<=24 hr) cold storage injury, with 6 or more glycerol monomers (n>=6) being generally preferred, and 10 or more monomers being most preferred (e.g., n=10 to 200) for simple cold storage.

The example of FIG. 1 underscores the lack of toxicity of even high concentrations (170 mOsm) of PGL during prolonged contact with living tissue. In the present application, this ability of polyglycerol to stabilize cell viability under conditions of reduced metabolism has been expanded by finding specific compositions containing polyglycerol that preserve not just tissue slices but also whole organs for prolonged periods, and that surprisingly do so more effectively that the best alternative organ preservation solution so far known in the art.

Figure 2:
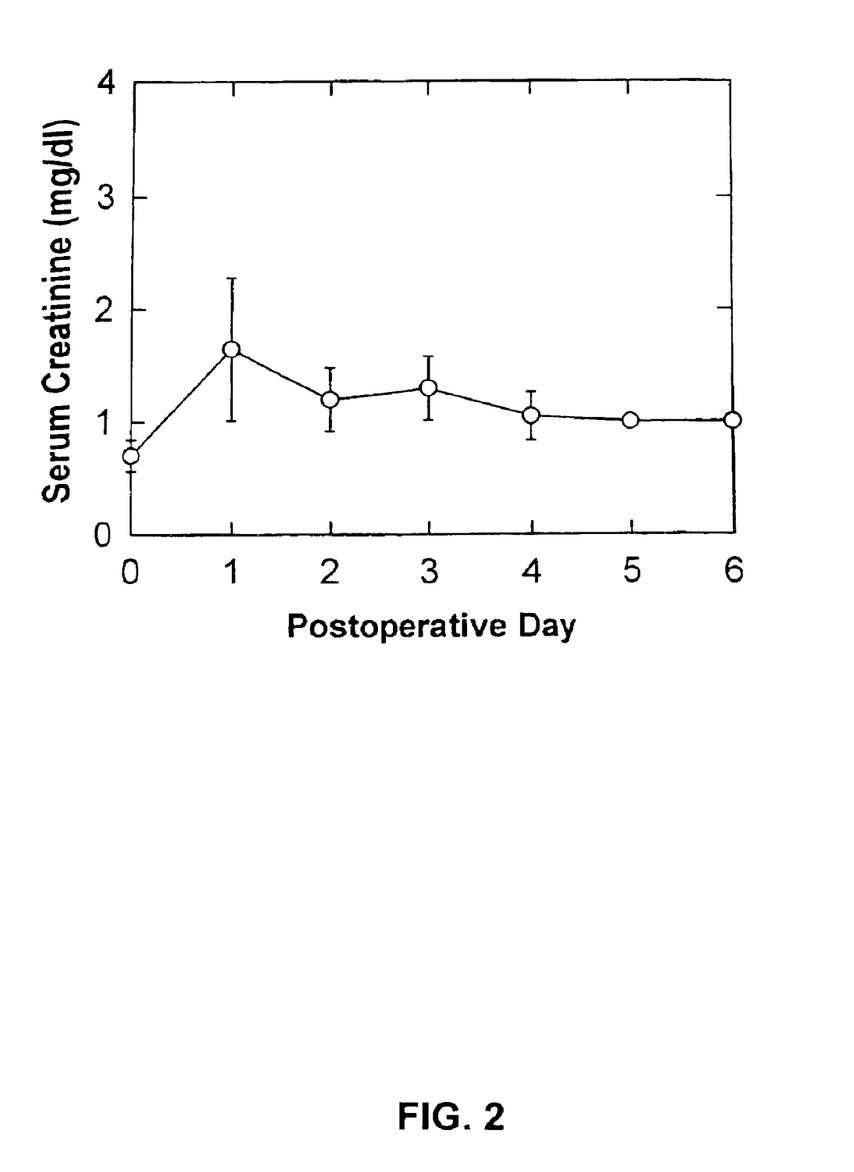
FIG. 2 shows the lack of toxicity of PGL used in a perfusate employed for the preservation of whole kidneys.

The lack of toxicity of a low concentration of PGL for a whole kidney was shown by perfusing two kidneys for 5 hours at about 3.5° C. with a solution known as LM5 (the formula for LM5 was as disclosed in U.S. Provisional application No. 60/221,691, filed Jul. $31^{st}$, 2000, and in U.S. patent application Ser. No. 09/916,396, filed Jul. $27^{th}$, 2001, both of which are herein incorporated by reference) to which was added 1% w/v decaglycerol and other non-toxic polymers. The kidneys were transplanted, and their recovery was measured by the postoperative serum creatinine levels attained. As indicated in FIG. 2, the postoperative functional recovery of these kidneys was good, showing the lack of toxicity of PGL for the vascular system during 5 hr of continuous perfusion and the applicability of PGL for use in perfusates, including perfusates designed to contain cryoprotectants that are made to vitrify with the assistance of the included PGL.

One embodiment of the preservation solution is a solution comprising lactose, with or without other additives. A further embodiment is a preservation solution comprising a combination of polyglycerol and lactose, with or without other valuable additives. This is illustrated by means of the following Examples, which demonstrate the efficacy of the invention. In addition, a method of preserving cells, tissues and organs using the disclosed preservation solutions at various temperature is disclosed. In addition, a method of rescuing and preserving cells, tissues, or organs using a solution comprising polyglycerol at higher temperatures, such as at room temperature or at body temperature, is disclosed.

As is shown in the examples which follow, polyglycerol and alpha lactose, two entirely novel candidate impermeants, were successfully tested and were found to have applications for conventional preservation. In particular, the use of alpha lactose or polyglycerol plus alpha lactose is useful for cell stabilization at about 0° C.±10° C. This includes isolated cells, cells in isolated tissues, or cells in organs. Polyglycerol is useful for the control of cell swelling at higher temperatures as well, for example in applications relating to stroke, shock, cardiac arrest, hypoxia, poisoning, head trauma, brain swelling, inflammation, and other conditions in which cell swelling may become an important pathological outcome.

The Examples show unequivocal maintenance of cell and organ integrity and indicate that the combination of polyglycerol plus lactose, with or without other efficacious additives, is useful for the hypothermic preservation of a wide range of cells from a wide range of species, and for the treatment of other states that, like hypothermia, result in an impaired ability of cells to offset their tendency to swell under conditions of impaired metabolism or impaired cell volume homeostasis.

EXAMPLES

Example 1

Lactose is Effective at Supporting Cellular Viability During Hypothermic Storage Table 1 shows that, in analogy to the results shown in FIG. 1, lactose can support the ion translocation capacity of rabbit renal cortical slices stored at 0° C.

TABLE 1

Exposure of Rabbit Renal Cortical Slices to Test Solutions at 0° C. for about 5 Hours[a]:

| Test solution | $K^+/Na^+$ |
|---|---|
| RPS-2 | 5.33 ± 0.20 |
| RPS-Lactose | 5.15 ± 0.22 |

[a]RPS-Lactose consists of RPS-2 in which about 175 mM glucose is replaced with an equal number of millimoles/liter of lactose. The difference between the groups is not significant, which means that lactose is an effective impermeant and is non-toxic to renal tissue.

Example 2

Figure 3:
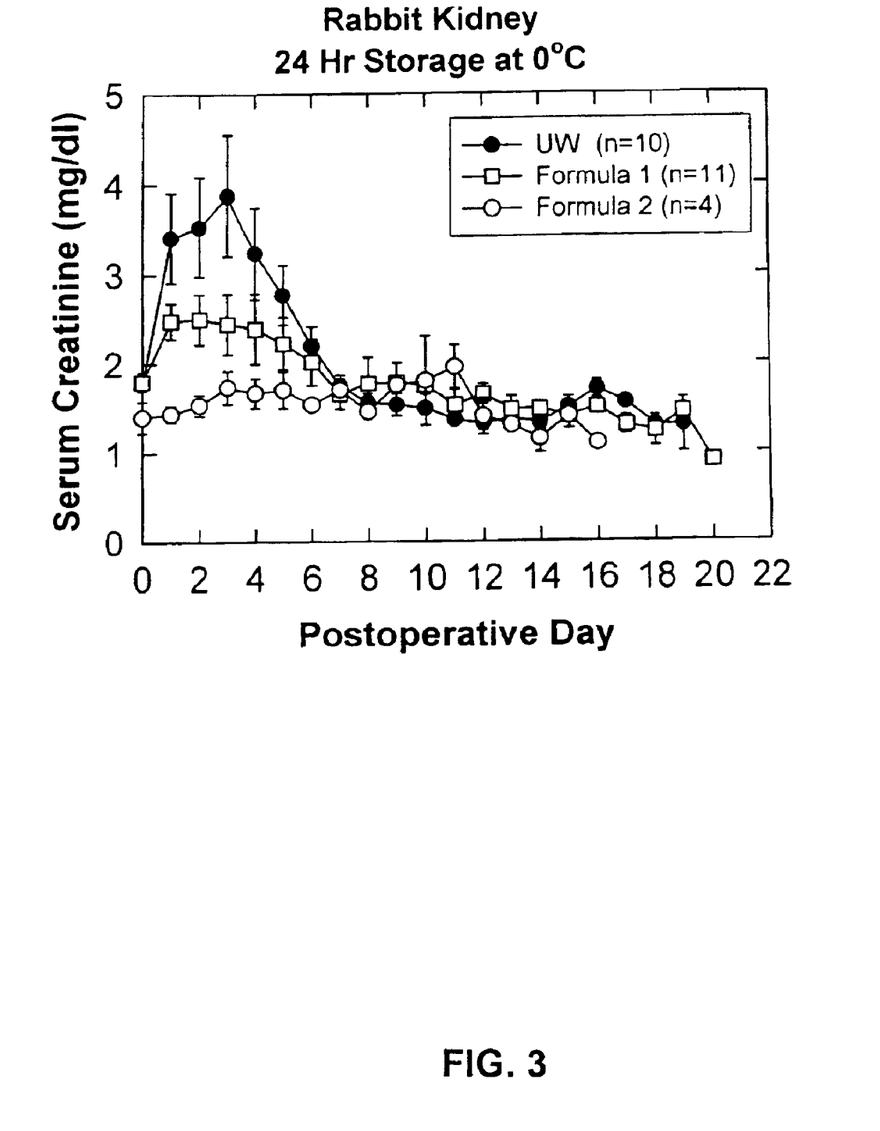
FIG. 3 shows postoperative serum creatinine levels in rabbits receiving kidneys preserved for 24 hrs at 0° C. with either solutions of the present invention or UW Solution (Viaspan).

Successful 24-hr Kidney Preservation with Polyglycerol/Lactose-containing Solutions FIG. 3 shows a comparison between the effects of 24 hrs of storage of rabbit kidneys at 0° C. after flushing with UW Solution, a preferred composition containing decaglycerol and alpha lactose (Formula 1), and a preferred composition containing decaglycerol, alpha lactose, and 5 micrograms/ml chlorpromazine (Formula 2; see Table 2 for the formulas of the solutions tested in FIG. 3) (means±1 SEM). We used chlorpromazine HCl for injection (Elkins-Sinn, Cherry Hill, N.J.) in these experiments. Kidney integrity was measured by following postoperative serum creatinine levels. The model involved removing and preserving the right kidney and transplanting it into the original donor at the site of the left kidney after storage, with removal and disposal of the left kidney at the time of transplantation. The ability of the model to detect and discriminate between different levels of reduced renal function was augmented by withholding hydration postoperatively, a maneuver which is believed to increase peak serum creatinine by about 2.5-fold.

In the experiments shown in FIG. 3, UW Solution was used exactly as directed by the manufacturer, and the UW Solution used was obtained from a vendor (Barr Laboratories, Pomona, N.Y.) to ensure authenticity. UW was washed out of the rabbit kidneys just prior to their transplantation using 20 ml of lactated Ringer's solution. Control experiments showed that this washout procedure did not affect the results of using Formula 1 and therefore the procedure appears innocuous. Formula 1 was used by incorporating chlorpromazine (50 micrograms/ml) into the first 50 ml of a flushing solution of Formula 1, and then washing the chlorpromazine out of the kidney prior to storage by using another 50 ml flush with Formula 1 devoid of chlorpromazine. In the case of Formula 2, the chlorpromazine was built into the solution and its concentration (5 micrograms/ml) was not different during flushing and during storage. Neither Formula 1 nor Formula 2 were washed out of the rabbit kidneys before transplantation.

Surprisingly, the kidneys preserved with polyglycerol-lactose solutions performed unequivocally better than those preserved with UW Solution (VIASPAN), and the best results were obtained when storage took place in the presence of the combination of decaglycerol, alpha lactose, and chlorpromazine, a combination which allowed essentially all injury to be effectively suppressed. A useful concentration range for chlorpromazine is 1–50 micrograms/ml, with the most preferred concentration range being 2–10 micrograms/ml. The superiority of chlorpromazine as an additive as in Formula 2 is surprising. But even without this additive, the decaglycerol-alpha lactose solution shown in FIG. 3 produced no postoperative serun creatinine values higher than 3.5, whereas over half of the transplants using UW Solution resulted in creatinines exceeding 4.0 (p<0.05 by Chi Square test). The p value for the comparison of the mean peak creatinines obtained with UW Solution and Formula 1 was 0.014. Since current clinical practice avoids the storage of human kidneys for more than 24 hrs prior to transplantation, superiority to UW Solution after 24 hrs of storage is of direct clinical significance. We are not aware of other solutions this superior to UW after 24 hr.

Furthermore, there appeared to be a defect in reabsorptive capacity on the part of UW Solution kidneys as compared to the decaglycerol/lactose kidneys, based on higher urine outputs, as determined from urine output scoring, in the face of higher serum creatinine concentrations on day 1 postoperatively in the UW group. This interpretation is supported by the clinical observation that the urine produced by experimental kidneys had a normal yellow color on day 1 whereas urine produced by UW-preserved kidneys appeared colorless, implying lack of concentration.

TABLE 2

Formulas for Some Preferred Embodiments of the Invention

| | Formula Number | | | | | | |
|---|---|---|---|---|---|---|---|
| | 1 | 1 | 2 | 2 | 3 | 3 | 4 |
| | Concentration Units | | | | | | |
| | mM or mOsm | g/liter | mM or MOsm | g/liter | mM or mOsm | g/liter | mM or mOsm |
| Physiologic support ingredients: | | | | | | | |
| Adenosine | 0 | 0 | 0 | 0 | 0 | 0 | 0 |
| Adenine HCl | 1 | 0.17 | 1 | 0.17 | 1 | 0.17 | 1 |
| Glutathione, reduced | 5 | 1.54 | 5 | 1.54 | 5 | 1.54 | 5 |
| Na-acetate*3H20 | 2 | 0.27 | 2 | 0.27 | 2 | 0.27 | 2 |
| $K_2HPO_4$*3H20 | 7 | 1.6 | 7 | 1.6 | 7 | 1.6 | 7 |
| $KH_2PO_4$ | 0 | 0 | 0 | 0 | 0 | 0 | 0 |
| NaCl | 40 | 2.34 | 40 | 2.34 | 40 | 2.34 | 40 |
| $CaCl_2$ | 1 | 0.111 | 1 | 0.111 | 1 | 0.111 | 1 |
| $MgCl_2$ | 1 | 0.095 | 1 | 0.095 | 1 | 0.095 | 1 |
| $MgSO_4$*(6H2O) | 0 | 0 | 0 | 0 | 0 | 0 | 0 |
| Impermeant ingredients: | | | | | | | |
| Glucose | 25 | 4.5 | 25 | 4.5 | 25 | 4.5 | 25 |
| 90% decaglycerol | ~62* | 20 | ~62* | 20 | ~62* | 20 | ~62* |
| Alpha lactose | 45 | 16.2 | 45 | 16.2 | 45 | 16.2 | 45 |
| Tripotassium citrate*$H_2O$ | 18 | 5.84 | 18 | 5.84 | 18 | 5.84 | 18 |
| HES (pentafraction) | 0 | 0 | 0 | 0 | 0 | 0 | 0 |
| Lactobionic acid | 0 | 0 | 0 | 0 | 0 | 0 | 0 |
| Raffinose pentahydrate | 0 | 0 | 0 | 0 | 0 | 0 | 0 |
| Special additives: | | | | | | | |
| Chondroitin sulfate A | 0 | 0 | 0 | 0 | ~20–200 $\mu M$ | 1 | 0 |
| Chlorpromazine HCl | 0 | 0 | 14 × $10^{-6}$ | 0.005 | 14 $\mu M$ | 0.005 | 14 $\mu M$ |
| Allopurinol | 0 | 0 | 0 | 0 | 0 | 0 | 0 |
| Potassium hydroxide | 0 | 0 | 0 | 0 | 0 | 0 | 0 |
| Penicillin G*** | 0 | 0 | 0 | 0 | 0 | 0 | 0 |
| Regular insulin*** | 0 | 0 | 0 | 0 | 0 | 0 | 0 |
| Dexamethasone*** | 0 | 0 | 0 | 0 | 0 | 0 | 41 $\mu M$ |
| Some solution characteristics: | | | | | | | |
| Total sodium | 42 | | 42 | | 42 | | 42 |
| Total potassium | 68 | | 68 | | 68 | | 68 |
| Total chloride | 41 | | 41 | | 41 | | 43 |
| Impermeant osmolality | 186 | | 186 | | 186 | | 186 |
| PGL/lactose ratio | 1.38 | | 1.38 | | 1.38 | | 1.38 |
| Total osmolality* | 300 | | 300 | | ~302 | | ~300 |
| adjust to pH: | 7.4 | | 7.4 | | 7.4 | | 7.4 |

| | Formula Number | | | | UW Solution | |
|---|---|---|---|---|---|---|
| | 4 | 5 | 5 | 6 | 6 | |
| | Concentration Units | | | | | |
| | g/liter | mM or mOsm | g/liter | mM or mOsm | g/liter | MM or mOsm | g/Liter |
| Physiologic support ingredients: | | | | | | | |
| Adenosine | 0 | 0 | 0 | 0 | 0 | 5 | 1.34 |
| Adenine HCl | 0.17 | 1 | 0.17 | 1 | 0.17 | 0 | 0 |
| Glutathione, reduced | 1.54 | 5 | 1.54 | 5 | 1.54 | 3 | 0.922** |
| Na-acetate*3H20 | 0.27 | 2 | 0.27 | 2 | 0.27 | 0 | 0 |
| $K_2HPO_4$*3H20 | 1.6 | 7 | 1.6 | 7 | 1.6 | 0 | 0 |
| $KH_2PO_4$ | 0 | 0 | 0 | 0 | 0 | 25 | 3.4 |
| NaCl | 2.34 | 55 | 3.21 | 70 | 4.09 | 0 | 0 |
| $CaCl_2$ | 0.111 | 1 | 0.111 | 1 | 0.111 | 0 | 0 |

TABLE 2-continued

| | | | | | | | |
|---|---|---|---|---|---|---|---|
| MgCl$_2$ | 0.095 | 2 | 0.19 | 2 | 0.19 | 0 | 0 |
| MgSO$_4$*(6H2O) | 0 | 0 | 0 | 0 | 0 | 5 | 1.23 |
| Impermeant ingredients: | | | | | | | |
| Glucose | 4.5 | 25 | 1.8 | 10 | 1.8 | 0 | 0 |
| 90% decaglycerol | 20 | ~31* | 10 | ~31* | 10 | 0 | 0 |
| Alpha lactose | 16.21 | 40 | 14.41 | 25 | 9.01 | 0 | 0 |
| Tripotassium citrate*H$_2$O | 5.84 | 20 | 6.49 | 20 | 6.49 | 0 | 0 |
| HES (pentafraction) | 0 | 0 | 0 | 0 | 0 | | 50 |
| Lactobionic acid | 0 | 0 | 0 | 0 | 0 | 100 | 35.83 |
| Raffinose pentahydrate | 0 | 0 | 0 | 0 | 0 | 30 | 17.83 |
| Special additives: | | | | | | | |
| Chondroitin sulfate A | 0 | 0 | 0 | 0 | 0 | 0 | 0 |
| Chlorpromazine HCl | 0.005 | 0 | 0 | 0 | 0 | 0 | 0 |
| Allopurinol | 0 | 0 | 0 | 0 | 0 | | 0.136 |
| Potassium hydroxide | 0 | 0 | 0 | 0 | 0 | 100 | 5.61 |
| Penicillin G*** | 0 | 0 | 0 | 0 | 0 | | 2 × 10$^5$ Units |
| Regular insulin*** | 0 | 0 | 0 | 0 | 0 | | 40 units |
| Dexamethasone*** | 0.016 | 0 | 0 | 0 | 0 | | 0.016 |
| Some solution characteristics: | | | | | | | |
| Total sodium | | 57 | | 72 | | 29 | |
| Total potassium | | 74 | | 74 | | 125 | |
| Total chloride | | 62 | | 77 | | 0 | |
| Impermeant osmolality | | 156 | | 126 | | ~230 | |
| PGL/lactose ratio | | 0.78 | | 1.24 | | NA | |
| Total osmolality* | | 300 | | 293 | | >320 | |
| adjust to pH: | | 7.4 | | 7.4 | | 7.4 | |

*Concentration in milli-osmoles/kg (mOsm)
**In UW Solution, "glutathione" = reduced glutathione plus oxidized glutathione.
***Must be added immediately prior to use, except for Formula 4.

Both of the solutions of the preferred embodiment in FIG. 3 contain 2% w/v decaglycerol, which imparts an osmotic contribution of about 62 mOsm, and 45 mM alpha lactose, which in principle adds about another 45 mOsm of impermeant osmotic pressure to the solution. The ratio of the osmotic contribution of decaglycerol to lactose is 62/45 = 1.38. Tripotassium citrate is present primarily as a buffer but is a nominal impermeant as well, which, although it is known to penetrate cells slowly, nominally contributes about ~54 mOsm and brings the total impermeant osmotic pressure to 161 mOsm. If one considers glucose, another nominal impermeant (a slowly-permeating solute) to be effectively impermeable over 24 hrs, its contribution of 25 mM brings the total impermeant concentration to 186 mOsm. The remaining components of the solution bring the total osmolality of the solution to 300 mOsm, which is close to the osmolality of blood. It is desirable to maintain a solution osmolality close to that of blood to avoid osmotic fluid shifts between the organ and blood at the time the preserved organ is transplanted.

The osmolality of blood is about 290 mOsm. A 10% increment or decrement from this value is acceptable, i.e., a reasonable tonicity range is 260–320 mOsm. At least one organ preservation solution in the past (Sack's solution) was successful for short-term preservation at total osmolalities of around 400 mOsm, but this is not desirable because when the organ is transplanted, water will shift from the blood to the organ, causing edema and reducing total blood flow. It is envisioned that the preferred upper limit of total osmolality is about 350 mOsm, or more preferably about 320–330 mOsm. Ringer's solution, which has been used for very short term (hours) preservation, has an osmolality of about 260 mOsm. A more preferred lower limit on total osmolality is believed to be about 270 or more preferably 280 mOsm, because a lower osmolality may cause cells to swell too extensively on contact, which reduces the ability of the organ to be perfused with the preservation solution and may slow initial blood reflow upon transplantation.

As noted above, the manufacturer's instructions for the UW Solution, which say to flush the kidney until the blood has been fully removed, were followed in the experiments depicted in FIG. 3. For the decaglycerol/lactose solutions, a standardized flush volume of 100 ml was used to avoid changing the volume established in the initial series involving 50 ml with chlorpromazine followed by 50 ml without chlorpromazine (Formula 1). This 100 ml volume was not required to flush all the blood from the kidney, but was used as a standard. However, with UW Solution, even 100 ml was frequently insufficient for complete blood washout. We recorded the time required to flush the kidneys with UW solution versus Formula 1, the volume of UW required for blood washout, and the mean flow rates (volume/time) for both solutions.

The results of these measurements on blood washout rates are given in Table 3.

TABLE 3

Faster and More Efficient Blood Washout with Lactose-Polyglycerol Solutions

| Solution | Flushing Rate | Time to Complete the Flush | Volume Used |
|---|---|---|---|
| UW Solution | 10.2 ± 0.62 ml/min | 12.3 ± 0.98 min | 125.6 ± 9.31 ml |
| Formula 1 | 18.1 ± 1.50 ml/min | 5.65 ± 0.44 min | 100.0 ± 0 ml |
| p value of difference | <.001 | <.001 | |

Means ± SEM.

Table 4 provides a comparison between the effects and properties of the new solutions described above versus those of UW Solution, the effects being summarized with respect to results obtained after storage for 24 hr.

TABLE 4

Comparison Between Decaglycerol-Alpha Lactose Solutions and UW Solution (VIASPAN), Including Functional Comparisons after 24 Hrs of 0° C. Storage

| Formulas 1 and 2 | UW Solution |
|---|---|
| 1. Low viscosity | 1. High viscosity |
| 2. Blood washout fast and easy | 2. Blood washout slow and difficult |
| 3. No additives before use | 3. Needs 3 additives before use |
| 4. No washout needed before transplant | 4. Must be washed out before transplant |
| 5. No early failure to reabsorb filtrate (early urine concentrated, yellow) | 5. Early defect in reabsorption (early urine dilute, watery) |
| 6. Consistently low serum creatinine | 6. Serum creatinine high in 5/9 cases |
| 7. Mild organ shrinkage | 7. Excessive organ shrinkage |
| 8. Inexpensive components that are easy to dissolve | 8. Expensive components that are hard to dissolve |
| 9. Easy to filter-sterilize | 9. Hard to filter-sterilize |
| 10. Approximately isosmotic to blood | 10. Hyperosmotic to blood |

Example 3

24-hr Preservation with Different Polyglycerol/Lactose Ratios

Figure 4:
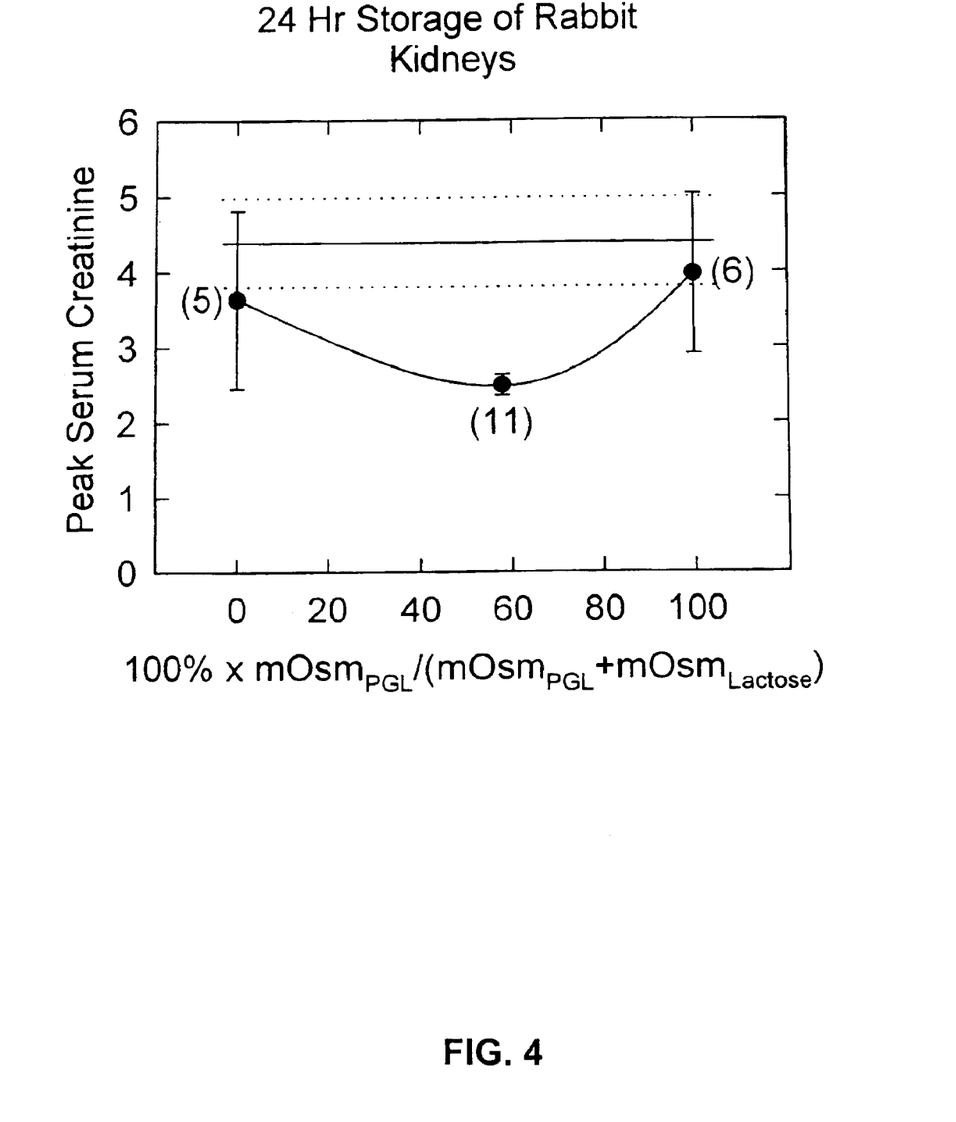
FIG. 4 shows postoperative serum creatinine levels in rabbits receiving kidneys preserved for 24 hrs at 0° C. with solutions comprising polyglycerol without lactose, lactose without polyglycerol, or a combination of polyglycerol and lactose.

FIG. 4 shows the results of using solutions containing polyglycerol only, lactose only, or both for 24 hr storage (means±SEM). These solutions were Formula 1 (middle point, at a PGL content of 57.9% of the total of (PGL+lactose) (n=11); Formula 1 minus lactose, with the amount of decaglycerol raised from the 18 grams/liter found in Formula 1 (20 grams of 90% decaglycerol stock=18 grams) to 32 grams/liter (35.5 g/l of 90% stock), total osmolality= 297 mOsm (point shown at 100% PGL, n=6); and Formula 1 minus decaglycerol, with the amount of lactose raised to 102 mM (point shown at 0% PGL, n=5), total osmolality= 300 mOsm. Intriguingly, although both the lactose-based solution and the decaglycerol-based solution yielded results equivalent to or better than UW solution (mean value for UW is represented as a solid horizontal line; dotted horizontal lines indicate plus and minus one standard error of the mean of 10 observations), only the mixture of PGL and lactose yielded a mean peak serum creatinine value that was statistically significantly different from UW solution (as noted above, p=0.014 for this comparison). The lactose-based solution yielded excellent results in 3 out of the 5 transplants (peak creatinines of 2–3, which is substantially better than with UW solution), but only the addition of PGL eliminated occasional high peak creatinines in a substantial number of trials (n=11). The reason for the special effectiveness of the combination of lactose and PGL is unknown, but the effect is clearly of practical importance.

Example 4

Successful 48-hr Preservation with Polyglycerol-lactose Solutions

Figure 5:
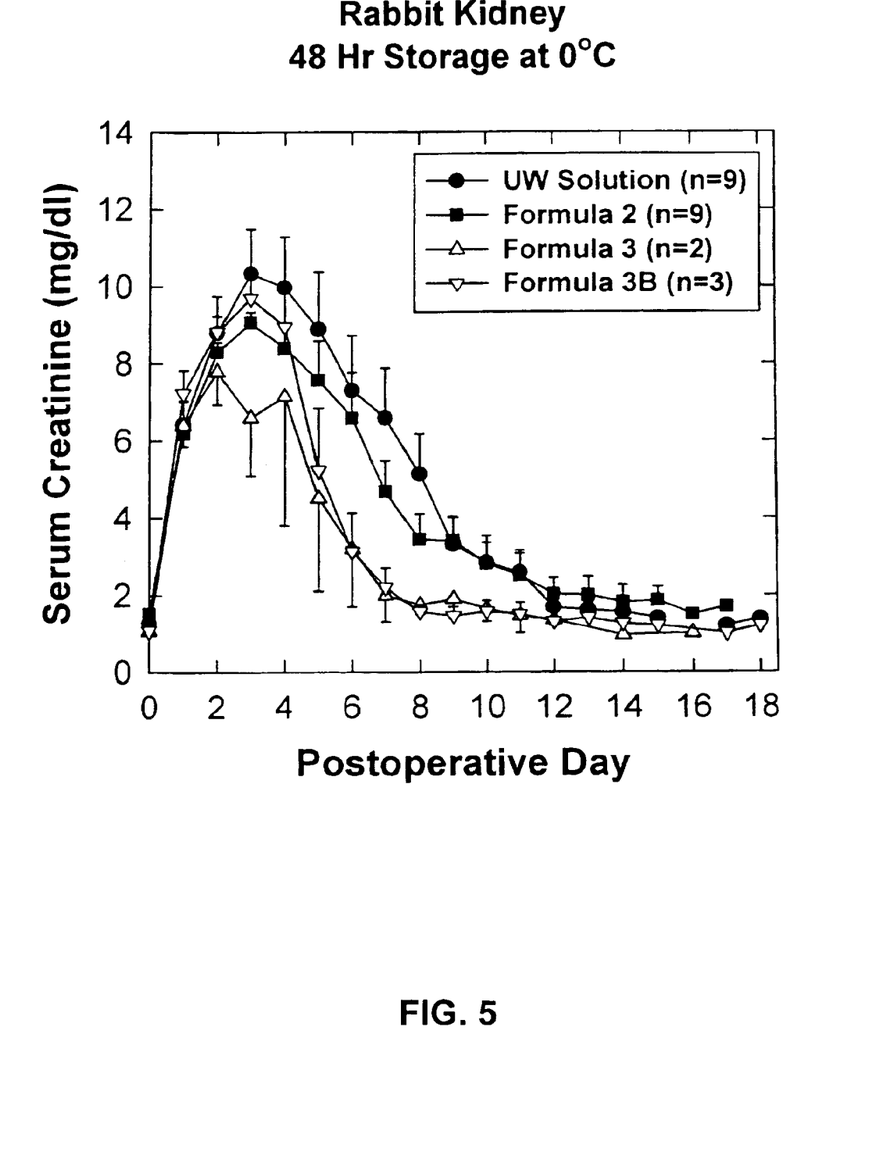
FIG. 5 shows postoperative serum creatinine levels in rabbits receiving kidneys preserved for 48 hrs at 0° C. with either solutions of the present invention or UW Solution.

All of the following experiments were carried out using a 48 hr storage period, but otherwise following the same transplantation protocol as described above. FIG. 5 shows a comparison between the effects of 48 hr of storage of rabbit kidneys at 0° C. after flushing with UW Solution, Formula 2, Formula 3, or Formula 3B. As noted in Table 2, Formula 3 was the same as Formula 2, except for the addition of 0.1% w/v chondroitin sulfate A (catalogue number C 8529, Sigma Chemical Company; 70% chondroitin sulfate A and 30% chondroitin sulfate C; 0.1% w/v is the total concentration of the mixture). Formula 3B is the same as Formula 3, except that the total concentration of chondroitin sulfate is 0.5% w/v rather than 0.1% w/v. The symbols in FIG. 5 represent means±1 standard error of the mean.

For recovery days 3–8, Formula 2 gave consistently lower serum creatinine levels than did UW Solution, though the differences were not statistically significant. Adding chondroitin sulfate (Formulas 3 and 3B) substantially shortened the time required to return creatinine to 2 mg/dl (12 days for UW Solution vs. 7 days for Formulas 3 and 3B). For this reason, by day 6, both concentrations of chondroitin sulfate resulted in mean serum creatinine levels that were about 60% lower than for UW Solution. Formula 3 also lowered mean peak creatinine values from over 10 for UW Solution to about 8. Based on these results, the range of useful concentrations of chondroitin sulfate extends from less than 0.1% w/v, such as 0.01% to 0.09%, to greater than 0.5%, such as 0.9% to 1% w/v. To our knowledge, no report of the successful use of chondroitin sulfate for organ preservation has ever appeared before.

We also tested the effects of adding dexamethasone (at 16 mg/liter) to Formula 2 (Formula 4, Table 2). The resulting curve of mean serum creatinine values after 48 hrs of storage was virtually superimposable on that of the Formula 2 curve shown in FIG. 5, but there was less variation from experiment to experiment, which is considered a desirable effect.

Clearly, at both 24 hrs and 48 hrs of preservation, there is a substantial advantage of the new lactose-polyglycerol solutions over the current industry standard,

Example 5

Effective Concentrations of Polyglycerol, Lactose, and Other Impermeants

Experiments were done to compare the results of storage for 48 hrs at 0° C. in lactose-polyglycerol solutions containing varying total impermeant species osmolalities (Formulas 1, 186 mOsm of impermeants; Formula 5, 156 mOsm of impermeants; and Formula 6, 126 mOsm of impermeants; see Table 2 for compositions). There were no statistically significant differences between the peak creatinine levels of the various groups despite wide variations in the total amount of impermeant species in the solution, nor did these groups differ significantly from UW Solution. This indicates that lactose-polyglycerol solutions can be effective over a considerable range of total impermeant species concentrations. If one considers that, after 48 hrs, glucose and citrate will have permeated fully, the range of acceptable concentrations of truly (not just nominally or temporarily) impermeant species concentrations is even broader than indicated above. For Formula 6, subtracting the contributions of citrate and glucose lowers total impermeant concentration from 126 mOsm to just 56 mOsm.

The preferred upper limit of the impermeants in the solution is about 250 mOsm, and even more preferably about 230 mOsm. The lowest limit of the impermeants in the solution is in principle about 20 mOsm, based on the classical observation that 20 mOsm is the approximate value for the total impermeable solute osmotic concentration in a typical cell. Thus, under idealistic conditions, the lower limit may be as low as 20 mOsm. Under more common conditions, the lower limit may be closer to 40 mOsm or, more preferably, about 50 mOsm, or, based on FIG. 6, as high as 126 mOsm, including 60, 70, 75, 80, 90, 100, 105, 110, 115, 120 and 125 mOsm. Thus, the permissible total concentrations of lactose or polyglycerol, when either species is present as the only impermeant, is about 20–250 mOsm when the solution is being used for hypothermic preservation of healthy cells, tissues, or organs.

When a solution of lactose or polyglycerol is being used to reverse warm ischemic injury, as in resuscitation following cardiac arrest, higher concentrations are generally appropriate. The typical upward osmotic pressure limit for a cell or a vascular bed, including the cerebral vasculature, is about 1500 mOsm. Therefore, for use in correcting ischemic injury, in which water may need to be withdrawn from swollen parenchymal and endothelial/vascular cells in order to restore tissue perfusion, a concentration of polyglycerol, lactose, or a combination of the two may be prepared and used such that, then the solution is diluted as a result of instillation into the area requiring assistance, its total concentration at the site of its action is up to 1500 mOsm.

Example 6

Efficacy of Formula 3 for Canine Kidney Preservation

Three canine kidneys were flushed with Formula 3 plus another ingredient and stored by simple cold storage. The rate of damage accumulation during cold storage was estimated based on serum creatinine levels, and this rate of damage accumulation (mg/dl of serum creatinine elevation per day of storage) was compared to the rate of damage accumulation for canine kidneys flushed with and stored in UW Solution plus the same extra ingredient. The result showed that the rate of damage accumulation in the Formula 3 group was essentially identical to that in the UW group, and there is no reason to believe that the extra ingredient affected this comparison. Thus, Formula 3 is equivalent to UW Solution in a canine model at least out to 48 hrs of cold storage at 0° C. From a practical point of view, this makes Formula 3 superior to UW, since Formula 3 is more convenient to use (see Table 4, which applies also to Formula 3 in regard to utilitarian aspects). The utility of Formula 3 for both canine kidneys and rabbit kidneys, and its superiority to UW for preserving rabbit kidneys, provides strong evidence that the formula will be effective for human kidney preservation to at least 48 hrs, which is a clinically very significant period, and supports the preferability of the solutions of the preferred embodiments to the use of UW Solution.

What is claimed is:

1. A solution for the liquid state hypothermic preservation of cells, tissues, and organs, said solution comprising a combination of polyglycerol and lactose, wherein the polyglycerol concentration falls in the range of 10 mOsm to 250 mOsm, and wherein the lactose concentration falls in the range of 11 mM to 250 mM.

2. The solution of claim 1 wherein the lactose comprises alpha-lactose.

3. The solution of claim 1 wherein the polyglycerol comprises from 2 to 200 monomer units.

4. The solution of claim 1 wherein the polyglycerol is decaglycerol or hexaglycerol.

5. The solution of claim 1 wherein the lactose concentration fall in the range of 20 mM to 150 mM.

6. The solution of claim 1 wherein the polyglycerol concentration falls in the range of 20 mOsm to 200 mOsm.

7. The solution of claim 1 further comprising glutathione.

8. The solution of claim 1, further comprising chondroitin sulfate.

9. The solution of claim 8 wherein the chondroitin sulfate is chondroitin sulfate A.

10. The solution of claim 8, wherein the concentration of chondroitin sulfate falls in the range of 0.01% w/v to 1% w/v.

11. The solution of claim 1, further comprising chlorpromazine.

12. The solution of claim 11, wherein the concentration of chlorpromazine is about 1–50 micrograms/ml.

13. The solution of claim 12, wherein the concentration of chlorpromazine is about 2–10 micrograms/ml.

14. The solution of claim 1, further comprising citrate.

15. The solution of claim 1, further comprising calcium.

16. The solution of claim 1, further comprising magnesium.

17. The solution of claim 1, further comprising adenine.

18. The solution of claim 1, further comprising glucose.

19. The solution of claim 1, further comprising acetate.

20. The solution of claim 1, further comprising phosphate buffer.

21. The solution of claim 1, wherein the solution has an osmolality of less than about 350 mOsm.

22. The solution of claim 1, further comprising citrate and glucose, wherein the sum of the osmotic contributions of polyglycerol, lactose, citrate and glucose to the solution is 20–250 mOsm (milliosmolal).

23. The solution of claim 1 wherein the osmotic concentration of the combination of polyglycerol and lactose falls in the range of 50 milliosmolal to 250 milliosmolal.

24. A method for the preservation of cells, tissues, or organs under conditions of impaired cell volume homeostasis, comprising:

contacting the cells, tissues, or organs with a solution of claim 1.

25. The method of claim 24 wherein the contacting is via intravenous or intra-arterial administration.

26. The method of claim 24 wherein the contacting is in vivo via arterial organ perfusion or retrograde venous perfusion of an organ or vascularized tissue.

27. The method of claim 24 wherein the contacting is in vitro via arterial organ perfusion or retrograde venous perfusion of an organ or vascularized tissue.

28. The method of claim 24 wherein the contacting is via the immersion of or bathing of affected cells, tissues, or organs.

29. The method of claim 24 wherein the polyglycerol comprises from 2 to 200 monomer units.

30. The method of claim 24 wherein the polyglycerol is tetraglycerol, hexaglycerol, or decaglycerol.

31. The method of claim 24 wherein the solution is an isotonic solution.

32. The method of claim 24 wherein the solution is a hypertonic solution.

\* \* \* \* \*